(12) United States Patent
Mori et al.

(10) Patent No.: US 6,556,925 B1
(45) Date of Patent: Apr. 29, 2003

(54) SIGNAL PROCESSING SYSTEM AND SIGNAL PROCESSING METHOD FOR CUTTING TOOL WITH ABRASION SENSOR

(75) Inventors: Kazuo Mori, Haga-gun (JP); Oleg Ryabov, Tsukuba (JP); Yoshio Nagato, Sendai (JP)

(73) Assignees: Kyocera Corporation, Kyoto (JP); Kajimura Koji, Tokyo (JP)

( * ) Notice: Subject to any disclaimer, the term of this patent is extended or adjusted under 35 U.S.C. 154(b) by 159 days.

(21) Appl. No.: 09/650,951

(22) Filed: Aug. 29, 2000

(30) Foreign Application Priority Data

Nov. 30, 1999 (JP) ............................. 11-339549

(51) Int. Cl.⁷ ............................................. G06F 19/00
(52) U.S. Cl. ......................................... 702/34; 702/81
(58) Field of Search ................... 702/34, 81; 304/511; 139/449; 340/453; 364/726, 575; 180/103; 382/152

(56) References Cited

U.S. PATENT DOCUMENTS

| | | | | |
|---|---|---|---|---|
| 3,908,782 A | * | 9/1975 | Lang et al. ................. | 180/103 |
| 4,351,029 A | * | 9/1982 | Maxey et al. ............... | 364/511 |
| 4,499,548 A | * | 2/1985 | Beebe ......................... | 327/91 |
| 5,318,077 A | * | 6/1994 | Yamashita ................... | 139/449 |
| 5,825,287 A | * | 10/1998 | Zarybnicky et al. ........ | 340/453 |
| 5,912,829 A | * | 6/1999 | Maier .................... | 364/726.02 |
| 6,249,599 B1 | * | 6/2001 | Kuroda ........................ | 382/152 |

FOREIGN PATENT DOCUMENTS

| | | | |
|---|---|---|---|
| JP | 187652 | * | 8/1986 |
| JP | 361187652 A | * | 8/1986 |
| JP | 3-120323 | | 12/1991 |
| JP | 9-038846 | | 2/1997 |

* cited by examiner

*Primary Examiner*—Michael Nghiem
*Assistant Examiner*—Tung Lau
(74) *Attorney, Agent, or Firm*—Hogan & Hartson, LLP (57) ABSTRACT

For determination of the expiration of the life of a cutting tool on the basis of a resistance signal from sensor lines, a true signal component indicative of the abrasion of the sensor lines should be extracted from the resistance signal. In a signal processing method according to the present invention, an output of an abrasion sensor is sampled in a predetermined sampling cycle (Step S1), and then the sampled data is passed through a median filter for elimination of a noise therefrom (Step S2). Further, the noise-free data is passed through a separation filter (Step S3). By the separation filter, reduction data having a time-serially reduced in value is separated and eliminated from the noise-free data. As a result, true data indicative of a change in the resistance of the sensor is obtained. The true data is subjected to a counter function process (Step S4) thereby to determine how many sensor lines have been cut off by the abrasion. The expiration of the life of the cutting tool is detected when the number of the cut-off sensor lines reaches a predetermined number (Step S5).

9 Claims, 13 Drawing Sheets

ADAPT DATA No.4 AS REPRESENTATIVE VALUE

ADAPT DATA No.3 AS REPRESENTATIVE VALUE

SIGNAL PROCESSING SYSTEM AND SIGNAL PROCESSING METHOD FOR CUTTING TOOL WITH ABRASION SENSOR

This application is based on an application No. 11-339549 filed in Japan, the content of which is incorporated herein by reference.

BACKGROUND OF THE INVENTION

1. Field of the Invention

The present invention relates to a signal processing system and a signal processing method for determining expiration of the life of a cutting tool to be used for cutting. Particularly, the invention relates to a system and a method for processing a signal obtained from an abrasion sensor provided on a cutting edge of a cutting tool.

2. Description of Related Art

Conventionally, an in-process tool abrasion diagnosis for detecting the abrasion and breakage of a cutting tool is based on indirect monitoring methods as described below:

(1) The abrasion is estimated on the basis of a change in a power or a cutting sound observed during a cutting process performed by a machine tool fitted with the cutting tool.

(2) A sensor for sensing an acoustic emission (AE) is provided adjacent a cutting edge of the cutting tool or on a tool holder, and occurrence of breakage and chipping is detected on the basis of an abnormal signal detected by the AE sensor.

In these indirect monitoring methods, the estimation of the abrasion is based on incidental physical phenomena such as the changes in the cutting force and the cutting sound and vibrations which occur incidentally to the abrasion and breakage of the cutting tool. Therefore, the indirect monitoring methods are less reliable with a poor measuring sensitivity. Further, the expiration of the life of the cutting tool is estimated at a lower level of accuracy, because the measurement results tend to include noises due to interference or the like.

One approach to these problems is described in Japanese Unexamined Utility Model Publication No. 3-120323 (1991). This publication discloses a throw-away tip having a sensor line of a conductive film provided along a cutting ridge on a flank thereof. It is also disclosed that the sensor line has a width conforming to an allowable abrasion width. In accordance with the throw-away tip disclosed in the publication, the sensor line is worn as the cutting ridge is worn, so that the expiration of the life of the cutting ridge can be detected when the sensor line is cut off.

Further, Japanese Unexamined Patent Publication No. 9-38846 (1997) proposes an ordinary cutting tool (not a throw-away tip) which has a thin film circuit on a flank thereof, wherein the expiration of the life of the cutting tool is automatically detected by sensing a change in electrical resistance which occurs due to abrasion of the thin film circuit as the flank is worn.

For the in-process tool diagnosis, the aforesaid method is preferred in which the sensor line is provided along the cutting ridge of the cutting tool to sense the change in the electrical resistance of the sensor line for the detection of the abrasion of the cutting ridge.

However, a resistance signal obtained from the sensor line during the cutting process is a fairly unstable signal which contains a noise and erroneous data. Therefore, it is important to extract a true signal component indicative of the abrasion of the sensor line from the resistance signal for determining the abrasion degree and breakage such as chipping of the cutting tool on the basis of the resistance signal from the sensor line.

SUMMARY OF THE INVENTION

To solve the aforesaid problems, it is an object of the present invention to provide a signal processing system and a signal processing method which are adapted to perform a signal processing operation on measurement data (sensor data) obtained from a cutting tool with an abrasion sensor to provide highly reliable process data.

In accordance with the present invention, a cutting tool has an abrasion sensor provided on a cutting edge thereof for detecting abrasion and breakage thereof occurring due to a cutting operation, and a resistance signal from the sensor which varies depending on the abrasion degree of the cutting tool is captured as a relatively roughly and discontinuously changing signal for determining the abrasion degree of the cutting tool at a discontinuous change point.

More specifically, the present invention has the following first to seventh inventive aspects.

In accordance with a first inventive aspect, there is provided a signal processing system for a cutting tool having an abrasion sensor provided on a cutting edge thereof for detecting abrasion and breakage thereof occurring due to a cutting operation, the signal processing system comprising: means for sampling an output of the abrasion sensor in a predetermined sampling cycle to obtain measurement data; noise eliminating means for eliminating a noise from the obtained measurement data; reduction data separating means for separating reduction data having a time-serially reduced value from the noise-free data; and life expiration determining means for determining an abrasion degree and breakage of the cutting tool on the basis of process data obtained by the separation of the reduction data.

In accordance with a second inventive aspect, the signal processing system according to the first aspect is characterized in that the noise eliminating means comprises median process means for outputting a median of a predetermined number of sampled data.

In accordance with a third inventive aspect, the signal processing system according to the first or second inventive aspect is characterized in that the abrasion sensor comprises a plurality of sensor lines extending parallel to each other along a cutting ridge of the cutting tool, and the life expiration determining means determines the abrasion degree and breakage of the cutting tool by relating the process data to the number of the sensor lines.

In accordance with a fourth inventive aspect, the signal processing system according to the third inventive aspect is characterized in that the life expiration determining means determines an initial resistance value of the plurality of sensor lines on the basis of an initial value of the process data, then determines a resistance threshold which is increased in response to cut-off of each of the sensor lines, and provides an output whenever a value of the process data exceeds the resistance threshold to indicate that the number of the cut-off sensor lines is increased.

In accordance with a fifth inventive aspect, the signal processing system according to any of the first to fourth inventive aspects is characterized in that the cutting tool comprises a throw-away tip provided with the abrasion sensor and a holder for holding the throw-away tip, and the abrasion sensor is capable of detecting the abrasion degree and breakage of the throw-away tip.

In accordance with a sixth inventive aspect, there is provided a signal processing method for a cutting tool having an abrasion sensor provided on a cutting edge thereof for detecting abrasion and breakage thereof occurring due to a cutting operation, the signal processing method comprising the steps of: sampling output data of the abrasion sensor in a predetermined sampling cycle; eliminating a noise from the sampled data; separating reduction data having a time-serially reduced value from the noise-free data; and determining an abrasion degree and breakage of the cutting tool on the basis of process data which is obtained by the separation of the reduction data and is free from time-serial reduction in value.

In accordance with a seventh inventive aspect, the method is characterized in that the abrasion sensor comprises a plurality of sensor lines extending parallel to each other along a cutting ridge of the cutting tool, and the process data has a value which increases time-serially stepwise by increments associated with the number of the sensor lines.

With the arrangements according to the first to sixth inventive aspects, the noise is eliminated from the sampled measurement data. The elimination of the noise can easily be achieved by performing the median process with the use of a median filter or the like as in the second inventive aspect.

The noise-free data is subjected to the data separation process with the use of a separation filter or the like. In the data separation process, the reduction data time-serially reduced in value is separated and eliminated from the noise-free data.

In general, the cutting edge of the cutting tool is abraded as the machining time increases. Since the sensor is accordingly abraded, the resistance increases. However, the reduction data time-serially reduced in value is included in the measurement data. This is supposedly attributable to erroneous data due to action of slugs and the like, because the cutting edge of the cutting tool is brought into contact with a workpiece to be cut thereby to be subjected to the slugs during the cutting operation. Therefore, the slugs of the workpiece hit against the cutting edge of the cutting tool or fuse on the cutting edge, thereby serving to reduce the resistance of the sensor. In the present invention, the data separation process is performed for the elimination of the reduction data time-serially reduced in value, so that only the data having a time-serially increased value is extracted as the process data.

The abrasion degree and breakage of the cutting tool is determined on the basis of the process data thus extracted.

As in the third, fourth and seventh inventive aspects, the determination of the abrasion degree and breakage of the cutting tool can advantageously be achieved by relating the process data to the number of the sensor lines. Where the sensor includes the plurality of sensor lines, the resistance of the sensor lines increases stepwise as the sensor lines are cut off one by one. In the course of the stepwise increase in the value of the process data, the cut-off of each of the sensor lines is detected at a time point at which the increase occurs. Therefore, the number of the sensor lines cut-off at a certain time point of measurement can be determined on the basis of the stepwise change in the resistance, whereby the abrasion degree of the cutting tool can be determined. The expiration of the life of the cutting tool can be detected when the predetermined number of sensor lines are cut off.

The present invention is preferably applied to the throw-away tip as in the fifth inventive aspect. However, the invention is applicable not only to the throw-away tip but also to a cutting tool having no replaceable cutting edge.

A specific embodiment of the present invention will hereinafter be described with reference to the attached drawings.

DESCRIPTION OF THE PREFERRED EMBODIMENT

In the following embodiment of the present invention, a throw-away tip to be described below is employed which functions as a cutting edge to be attached to a holder or the like. However, it should be understood that the present invention can be applied to ordinary cutting tools other than the throw-away tip in the same manner.

Figure 1:
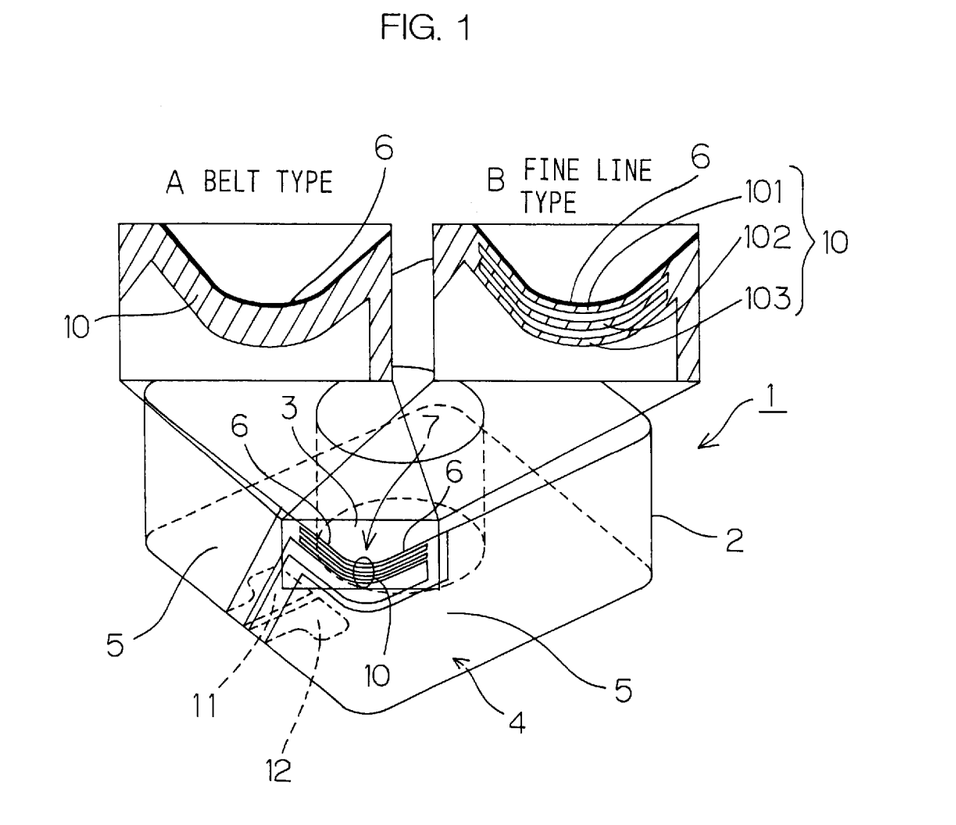
FIG. 1 is a diagram illustrating a throw-away tip 1 as an exemplary cutting tool with an abrasion sensor.

FIG. 1 is a diagram illustrating the throw-away tip 1 provided with an abrasion sensor as an exemplary cutting tool with an abrasion sensor.

The throw-away tip 1 has a base 2 of a generally rectangular column shape. An upper face of the base 2 defines a rake face 3, while a lower surface of the base 2 defines a seat face 4. Side faces of the base 2 define flanks 5, and intersections between the rake face 3 and the flanks 5 define cutting ridges 6. Further, the rake face 3 and each two adjacent flanks 5 define a corner portion 7 to be used for cutting.

A sensor line 10 of a conductive film is provided on the corner portion 7 as extending along the cutting ridges 6. As shown in fragmentary enlarged diagrams A and B, the sensor line 10 extends along the cutting ridges 6 in parallel relation as surrounding the corner portion 7 on the two adjacent flanks 5 defining the corner portion 7. The sensor line 10 may be a single belt-shaped sensor line as shown in the fragmentary enlarged diagram A, or may include, for example, three fine lines 101, 102, 103 which extend parallel to each other and are connected to each other in parallel at opposite ends thereof as shown in the fragmentary enlarged diagram B.

During monitoring of the cutting process, the sensor line 10 is gradually abraded from a portion thereof adjacent to the cutting ridges 6 thereby to be thinned, as the abrasion of the flanks 5 proceeds. Where the sensor line 10 is constituted by the three fine lines, the fine line 101 which is the closest to the cutting ridges 6, and then the fine lines 102, 103 are successively cut off in this order. Therefore, the electrical resistance of the sensor line 10 as measured at opposite ends thereof is accordingly increased in a discontinuous manner. The number of times of the discontinuous increase in the electrical resistance which can be determined through signal processing corresponds to the number of cut-off fine lines, so that the abrasion width of the flanks 5 can be determined in the process. Where the sensor line 10 is of the belt type, the expiration of the life of the cutting ridges can be detected when the resistance becomes the infinity.

As described in the prior art, the direct detection of the abrasion degree based on the change in the electrical resistance of the conductive material provided on the tool has conventionally been proposed. However, the conventional methods are adapted to directly determine the abrasion degree on the basis of the resistance of the system including the workpiece. Therefore, it is difficult to determine the abrasion degree at a high level of accuracy on the basis of a resistance signal including an unstable factor due to intermittent shorting and contact resistance between the workpiece and the sensor.

In the present invention, an attempt is made to obtain more accurate information even from a low S/N ratio signal by causing the resistance signal to have a relatively rough and discontinuous change in accordance with the abrasion degree, as will be described in detail by way of the following embodiment. That is, the detection of the abrasion is based on detection of a change in a signal pattern without utilizing the resistance itself. Thus, reliable information can be obtained from the unstable signal, though a measurement resolution is sacrificed to some extent.

In the throw-away tip 1 shown in FIG. 1, the sensor line 10 is connected to contact regions 11, 12 provided on the seat face 4. The contact regions 11, 12 are brought into contact with probes of a detection circuit for detection of the resistance of the sensor line 10.

An explanation will hereinafter be given to the construction of the sensor line 10 having the three fine lines 101, 102, 103 shown in the fragmentary enlarged diagram B.

In the meanwhile, where the sensor line 10 is constituted by the single belt-shaped line as shown in the fragmentary enlarged diagram A, the belt-shaped sensor line 10 preferably has a width which conforms to a reference life of the corner portion 7 (an allowable abrasion limit of the flanks 5). Where the life is to expire when the flanks 5 of the throw-away tip 1 is abraded to a width of 0.2 mm, the sensor line 10 is formed to have a width of 0.2 mm. When the cutting process with the use of the corner portion 7 is in progress, the cutting ridges 6 and the flanks 5 are abraded as the machining time increases. When the abrasion width of the flanks 5 exceeds the allowable abrasion limit for the reference life, the sensor line 10 having the width conforming to the reference life is cut off by the abrasion. Since the resistance of the sensor line 10 measured at its opposite ends is changed from a finite value to the infinity, the expiration of the life of the corner portion 7 is detected on the basis of so-called binary information.

Figure 2:
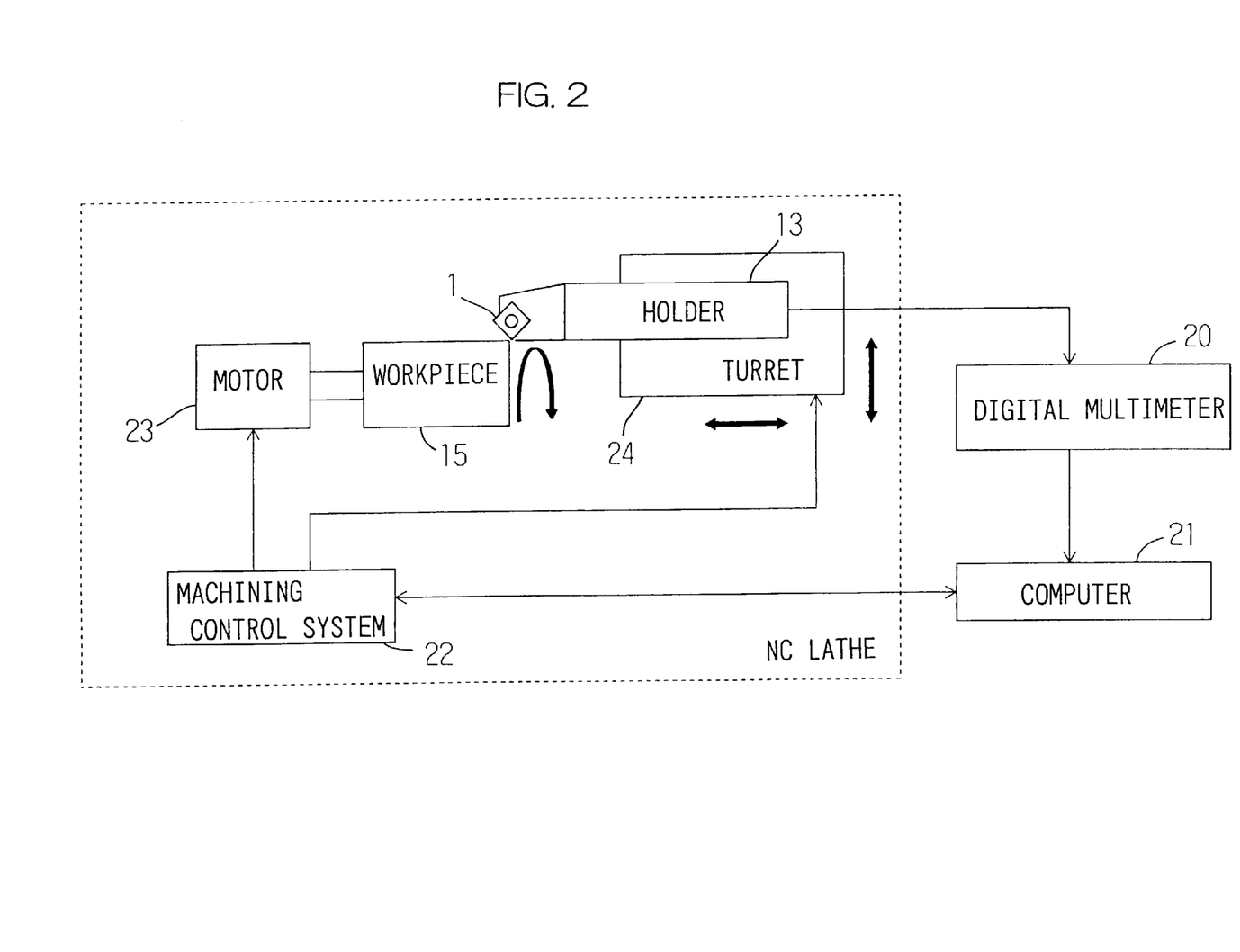
FIG. 2 is a block diagram illustrating the construction of a signal processing system for the throw-away tip 1 with the abrasion sensor in accordance with one embodiment of the invention.

FIG. 2 is a block diagram illustrating the construction of a signal processing system for the throw-away tip 1 with the abrasion sensor in accordance with one embodiment of the invention. A sensor signal (resistance) of the throw-away tip 1 mounted on an NC lathe is applied to a digital multimeter 20 via signal lines and the like in a holder 13. In the digital multimeter 20, the resistance is converted into a digital signal, which is outputted to a computer 21. The computer 21 is the core of the signal processing system, and performs a predetermined signal processing operation to be described later. An output of the computer 21 is applied to a machining control system 22 of the NC lathe. As a result, a motor 23 for turning a workpiece 15 and a turret 24 for controlling the cutting depth and length of the workpiece 15 are controlled to be stopped as required by the machining control system 22.

Figure 3:
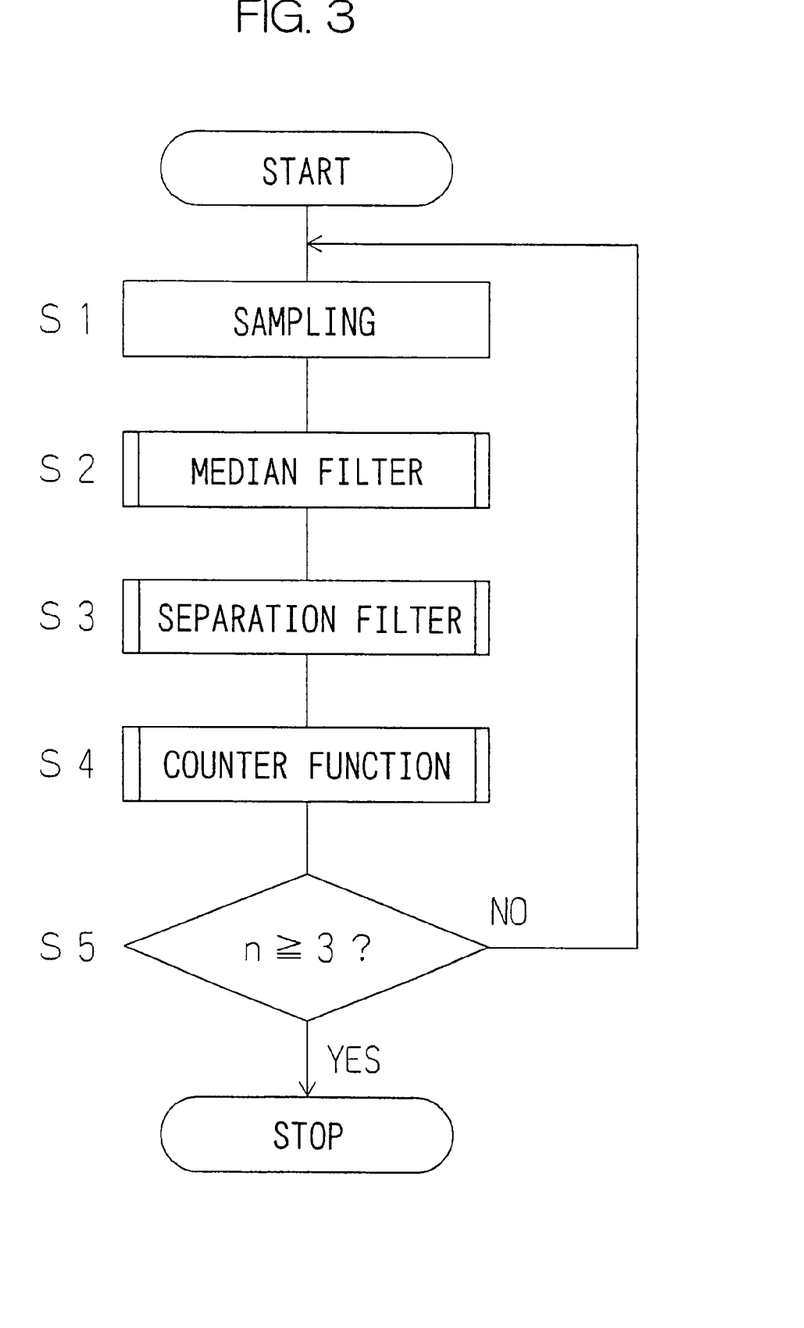
FIG. 3 is a flow chart illustrating a control process to be performed by a computer 21.

FIG. 3 is a flow chart illustrating a control process to be performed by the computer 21 in FIG. 2. In the control process, resistance measurement data applied in the form of a digital signal from the digital multimeter 20 is sampled in a predetermined sampling cycle (Step S1). In this embodiment, the sampling cycle is set at 1 second in consideration of the fact that the corner portion 7 of the throw-away tip 1 has a life of about 3000 seconds. The sampling cycle may properly be set in accordance with the types of the cutting tool and the workpiece to be employed. Where the sampling cycle is set at 1 second as in this embodiment, the number of process data is reduced, so that the signal processing operation can be performed at a relatively high speed with the use of a smaller capacity memory. That is, the signal processing system can be constructed by employing a less expensive computer 21 (microprocessor).

Figure 4:
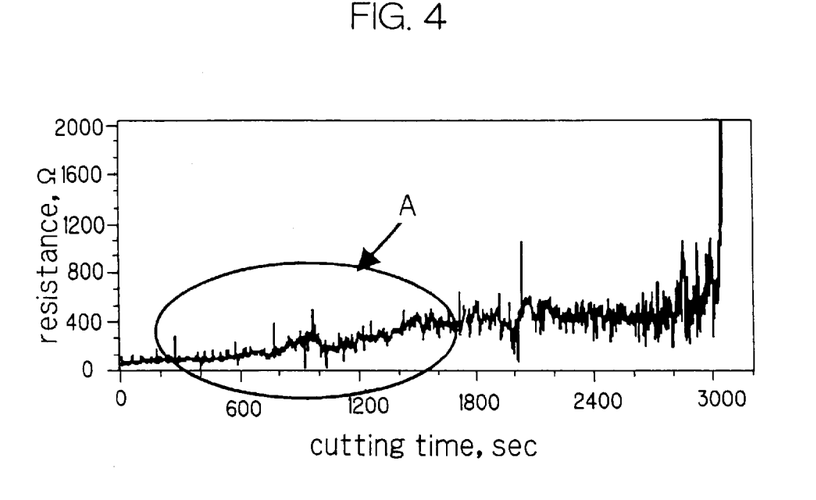
FIG. 4 is a diagram illustrating an example of sampled measurement data.

An example of the measurement data sampled in Step S1 is shown in FIG. 4. The sampled data is a signal indicative of the resistance which jaggedly fluctuates and includes a noise component.

In Step S2, the sampled data is passed through a median filter for elimination of the noise therefrom.

In Step S3, the noise-free data is passed through a separation filter for elimination of reduction data having a time-serially reduced value therefrom.

In Step S4, process data excluding the reduction data is applied to a predetermined counter function to determine how many fine lines of the three fine lines 101, 102, 103 of the sensor line 10 have been cut off.

As a result, the abrasion degree of the throw-away tip at the time point of the measurement can be determined on the basis of the number of the cut-off fine lines. When all the three fine lines 101, 102, 103 are cut off, the sensor line 10 is completely cut off, indicating the expiration of the life (YES in Step S5). A signal indicative of the expiration of the life is applied to the machining control system 22 of the NC lathe.

On the basis of the applied signal, the machining control system 22 performs necessary operations, i.e., stops the motor 23 to stop turning the workpiece 15, and moves the turret 24 to bring the throw-away tip 1 away from the workpiece 15.

Further, the expiration of the life of the cutting ridges of the throw-away tip 1 is reported to an administrator of the NC lathe.

Steps S2, S3 and S4 shown in FIG. 3 will next be described one by one in detail.

Median Process (Step S2)

In a median process, a median of each group of a predetermined number of sampled data is outputted. This process is achieved with the use of a known filter called "median filter".

Figure 5A:
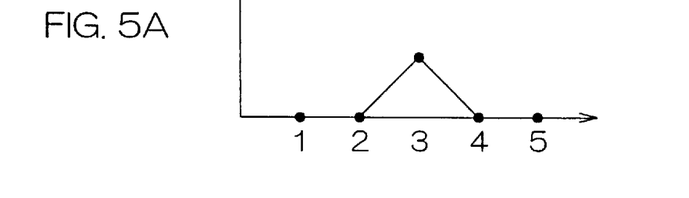
FIGS. 5A and 5B are schematic diagrams for explaining a median filtering process.
Figure 5B:
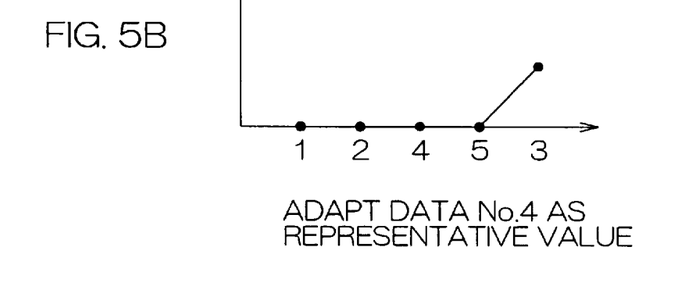

The number m of the data to be processed in a group by the median filter at a time is herein assumed to be m=5. When sampled data No. 1 to No. 5 are applied to the median filter as shown in FIG. 5A, the median filter rearranges the five data in increasing order of data value as shown in FIG. 5B. Then, the data No. 4 in the median of the five data arranged in increasing order is outputted as a representative value of the data group.

Figure 6A:
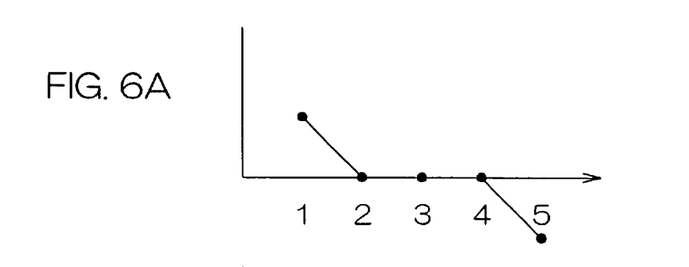
FIGS. 6A and 6B is a schematic diagram for explaining another example of the median filtering process.
Figure 6B:
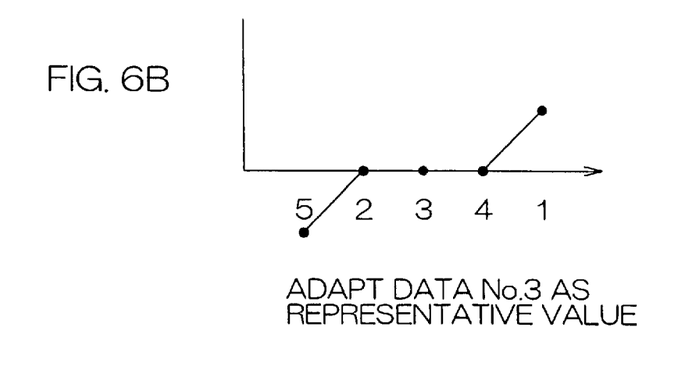

In another case where a group of data No. 1 to No. 5 as shown in FIG. 6A are applied, the five data are rearranged in increasing order of data value as shown in FIG. 6B. Then, the data No. 3 in the median is outputted as a representative value of the data group.

In the median filtering process, the median of each sampled data group is outputted, whereby abnormal data values such as extraordinarily great or small data values can be eliminated.

Figure 7:
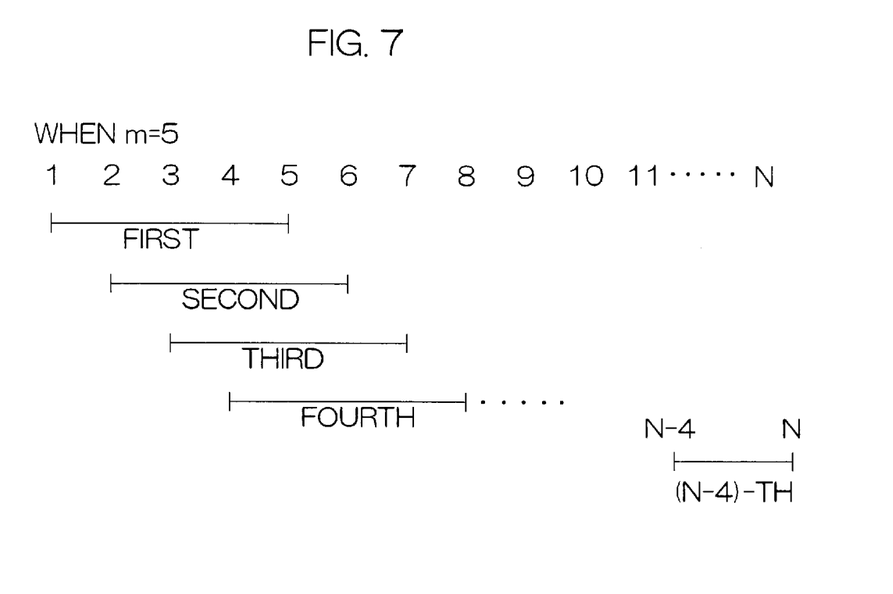
FIG. 7 is a diagram for explaining the shift of a data group to be processed by a median filter.

As shown in FIG. 7, sampled digital data No. 1, No. 2, No. 3, No. 4, . . . , No. N are sequentially applied to the median filter. Where the median filter is adapted to output the median of every five data (m=5), the median filter outputs firstly the median of a group of the data No. 1 to No. 5, secondly the median of a group of the data No. 2 to No. 6, thirdly the median of a group of the data No. 3 to No. 7, and so forth. That is, data to be employed for the provision of the median are shifted one by one, and the medians thus provided are successively outputted.

Figure 8:
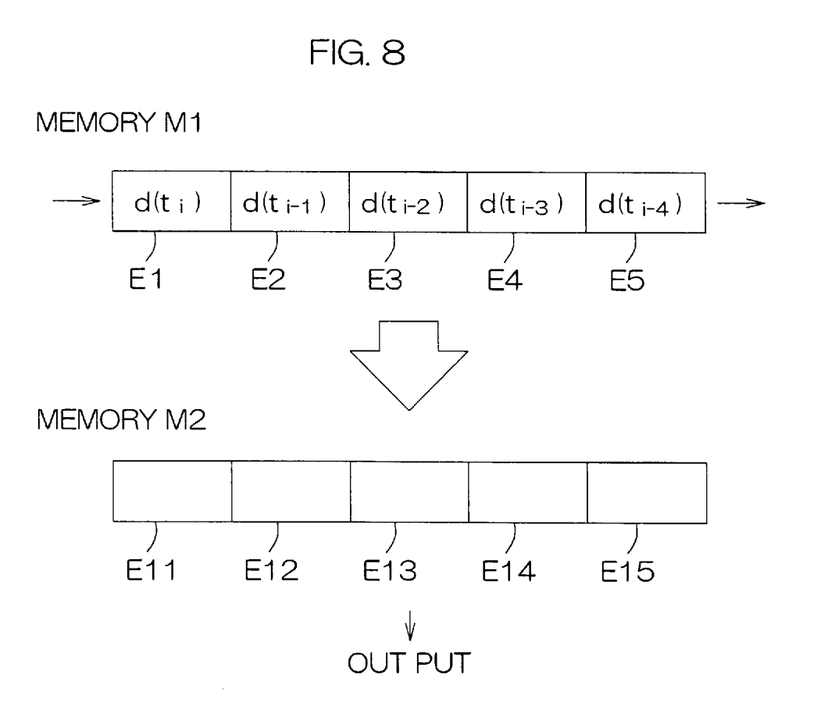
FIG. 8 is a diagram illustrating an example of two memories constituting the median filter.

The median filter operative in such a manner can easily be constructed by employing two memories M1, M2 as shown in FIG. 8. In FIG. 8, the memory M1 is adapted to store five sampled data in chronological order, and has five memory areas E1 to E5. The latest sampled data $d(t_i)$, the second latest sampled data $d(t_{i-1})$, the third latest sampled data $d(t_{i-2})$, the fourth latest sampled data $d(t_{i-3})$ and the fifth latest sampled data $d(t_{i-4})$ (wherein i is a natural number, i=1, 2, 3, . . . , N) are stored in the memory areas E1, E2, E3, E4 and E5, respectively. Upon completion of each process, the data in the memory areas E1 to E5 are shifted to the right by one, so that the latest sampled data is stored in the memory area E1. This memory M1 is comprised, for example, of a FIFO memory.

The memory M2 is used for sorting the five sampled data $d(t_i)$ to $d(t_{i-4})$ stored in the memory M1 in increasing order of data value to rearrange the data. The memory M2 has memory areas E11 to E15 for storing the sorted data. The sampled data sorted in increasing order are stored in the memory areas E11 to E15 in series, so that the median of the five sampled data is stored in the memory area E13. Therefore, the data stored in the memory area E13 is outputted as a representative value.

Figure 9:
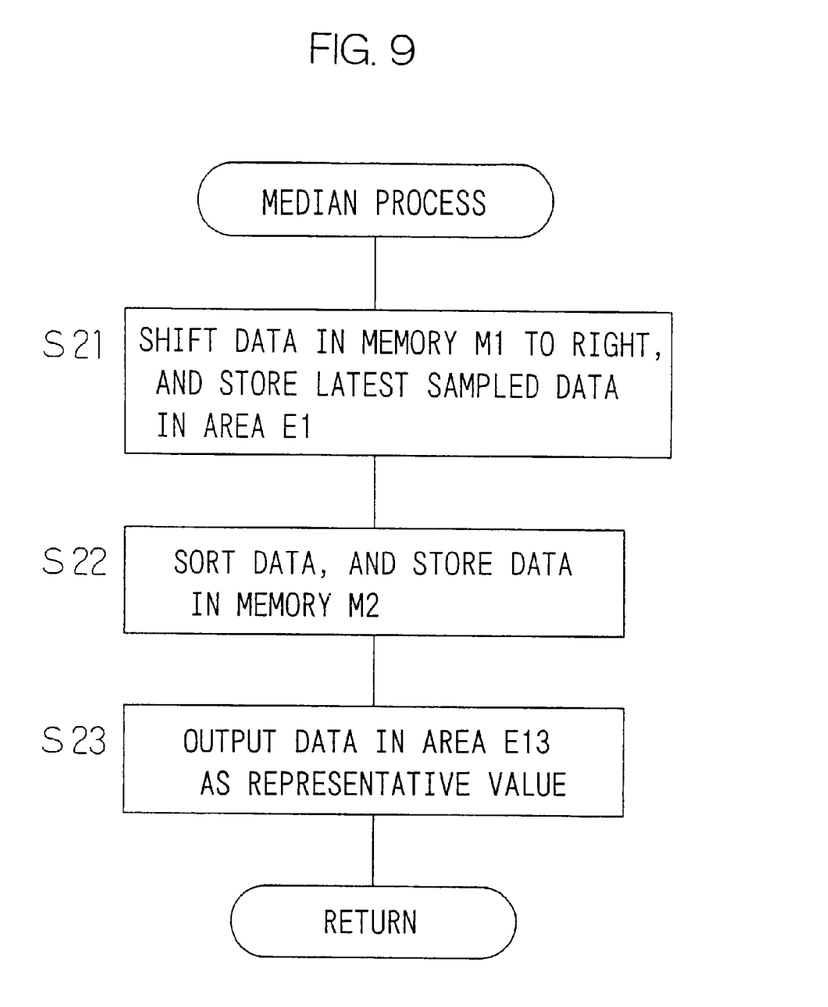
FIG. 9 is a flow chart illustrating the median process employing the memories shown in FIG. 8.

This process is illustrated in a flow chart in FIG. 9. The operation to be performed by the median filter will be described in conjunction with the following mathematical expressions.

Provided that the sampled resistance measurement is d(t), the data fd obtained through the filtering process by the median filter is expressed as follows:

$$fd(t_i) = \Phi^m(d(t_i)), \quad i=\overline{1,N-m} \quad (1)$$

wherein ti is an i-th filtering time frame, N is the total number of data d(t), and $\Phi^m$ is a median filter function for a size m (m=5 in this embodiment) and is expressed as follows:

$$\Phi^m(X_i) = X_j, \quad X_k, \ldots, X_{k+n} < X_j < X_1, \ldots, X_{1+n}, \quad \forall X \in [X_i, X_{i+m}] \quad (2)$$

Figure 10:
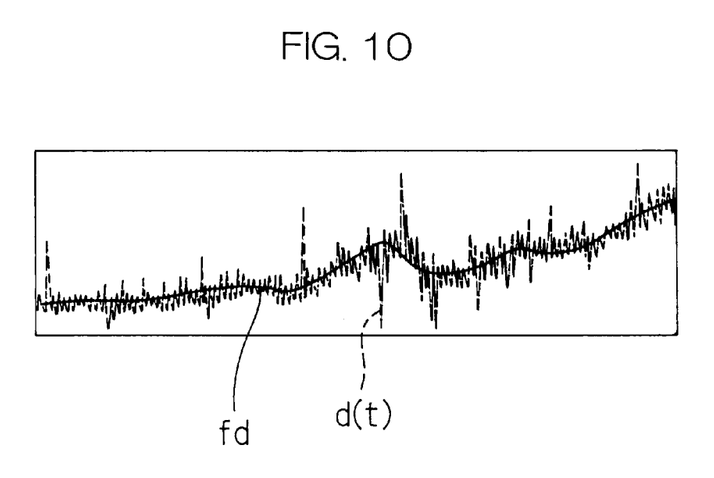
FIG. 10 is a diagram illustrating an example of data filtered by the median filter.

An example of the data obtained through the filtering process by the median filter is shown in FIG. 10, which is an enlarged diagram of a portion A in FIG. 4. In FIG. 10, the sampled source data d(t) is indicated by a broken line, and the noise-free data fd obtained through the filtering by the median filter is indicated by a solid line. As can be seen from FIG. 10, the median process provides a smooth data profile which is free from random noises.

Separation Filtering Process (Step S3)

The separation process to be performed by the separation filter is essential to extract a true resistance value from the data obtained through the median filtering process. The most critical factor causing the fluctuation of the resistance of the sensor line 10 is a short intermittently occurring during the cutting of the workpiece. That is, the corner portion 7 of the throw-away tip 1 is kept in contact with the workpiece, and subjected to slugs generated at the cutting. Therefore, the slugs hit against or fuse on the corner portion around the sensor line 10, so that the resistance is fluctuated. Since the workpiece is typically composed of a conductive metal, the slugs thereof hitting against or adhering on the corner portion 7 reduce the resistance of the sensor line 10.

Actually, the resistance of the sensor line 10 increases due to the abrasion of the corner portion 7 as the machining time increases. This suggests that data having a reduced value is false and data having an increased value is true among the data time-serially provided. Therefore, the reduction data time-serially reduced in value is separated and eliminated from the data obtained through the median process, and only resistance data time-serially increased in value is extracted in the separation filtering process. That is, a true value tdd of the resistance which varies with the abrasion of the throw-away tip is expressed as follows:

$$tdd(t_i) = \Pi(fd(t_i)), \quad \Pi(\chi_i) = \begin{cases} \chi_i, & \text{if } \chi_i \geq \chi_{i-1} \\ \chi_{i-1}, & \text{if } \chi_i < \chi_{i-1} \end{cases} \quad (3)$$

wherein $\Pi$ is a separation operator.

Figure 11:
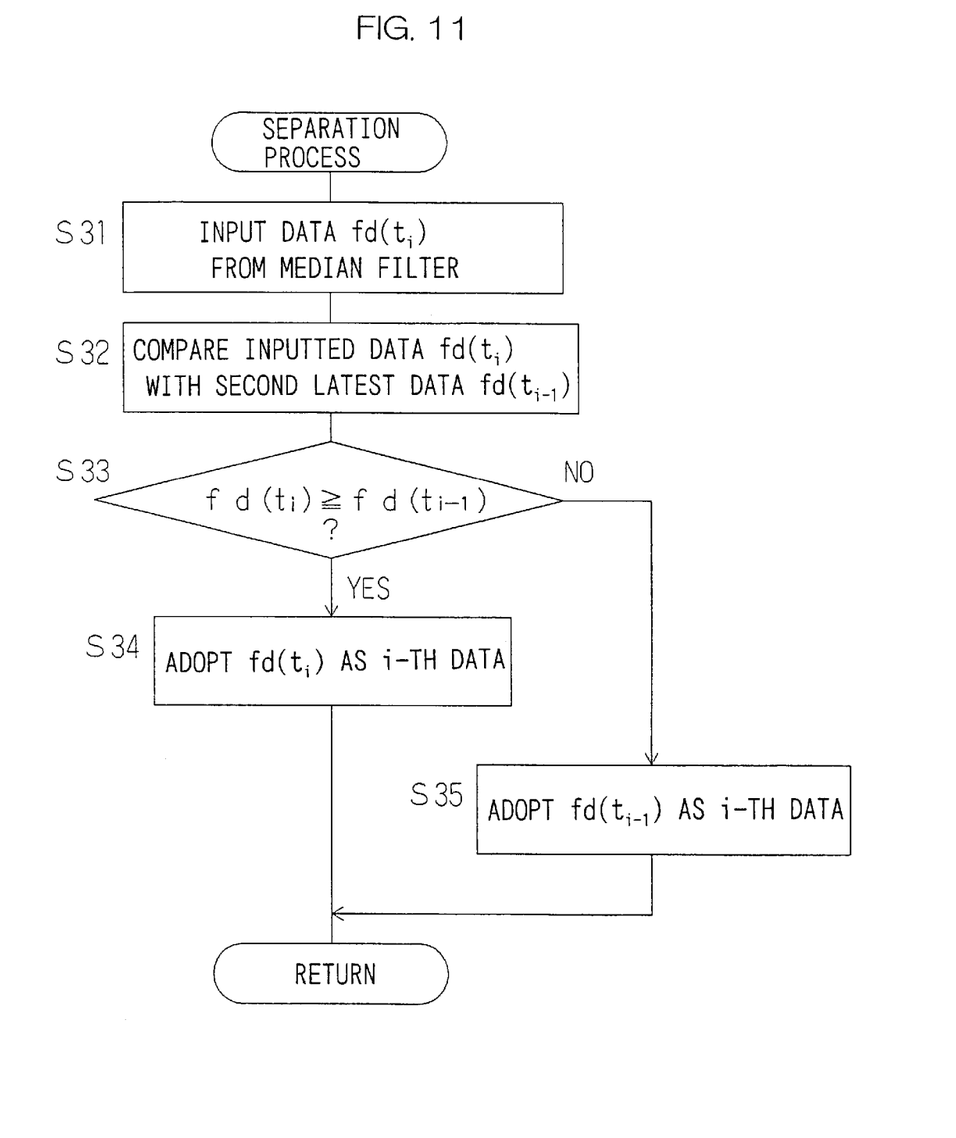
FIG. 11 is a flow chart illustrating specific operations of a separation process.

FIG. 11 is a flowchart illustrating the separation process to be performed by the separation filter. The data obtained through the filtering process by the median filter are sequentially applied to the separation filter. When data $fd(t_i)$ is inputted to the separation filter from the median filter (Step S31), the value of the inputted data $fd(t_i)$ is compared with the value of the (i−1)-th data $fd(t_{i-1})$ adopted immediately before the inputted data (Step S32).

If the comparison result is $fd(t_i) \geq fd(t_{i-1})$ (YES in Step S33), the inputted data $fd(t_i)$ is adopted as the i-th data (Step S34).

If NO in Step S33, the data $fd(t_{i-1})$ compared with the inputted data is adopted as the i-th data (Step S35).

This process is repeated, whereby the data No. 1 to No. N are adopted in time series.

Figure 12:
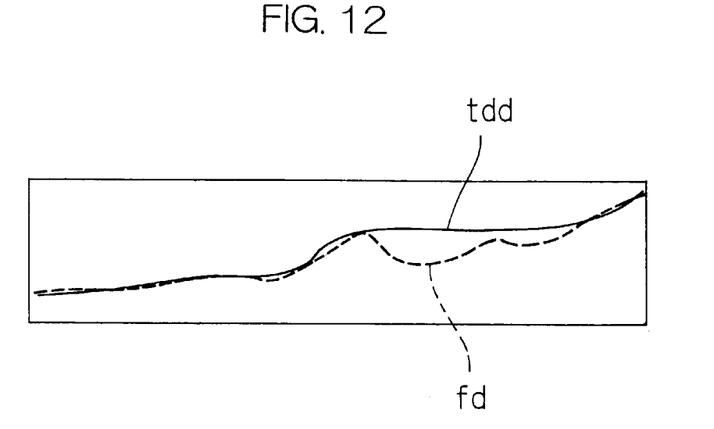
FIG. 12 is a diagram illustrating an example of data obtained through the separation process.

Through this process, the data tdd indicated by a solid line in FIG. 12 is obtained. In FIG. 12, the data fd obtained through the median filtering process shown in FIG. 10 is indicated by a broken line. By passing the data fd through the separation filter, the data tdd indicated by the solid line are provided.

Counter Function Process (Step S4)

Where the sensor line 10 of the throw-away tip 1 is constituted by the three fine lines 101, 102, 103 as shown in FIG. 1, the abrasion degree at a time point of the measurement can be estimated from the predetermined number and configuration of the fine lines by counting the number of the cut-off fine lines. That is, it is merely necessary to count the number of the times of the step-wise increase in the resistance which occurs due to the cut-off of the fine lines.

Figure 13:
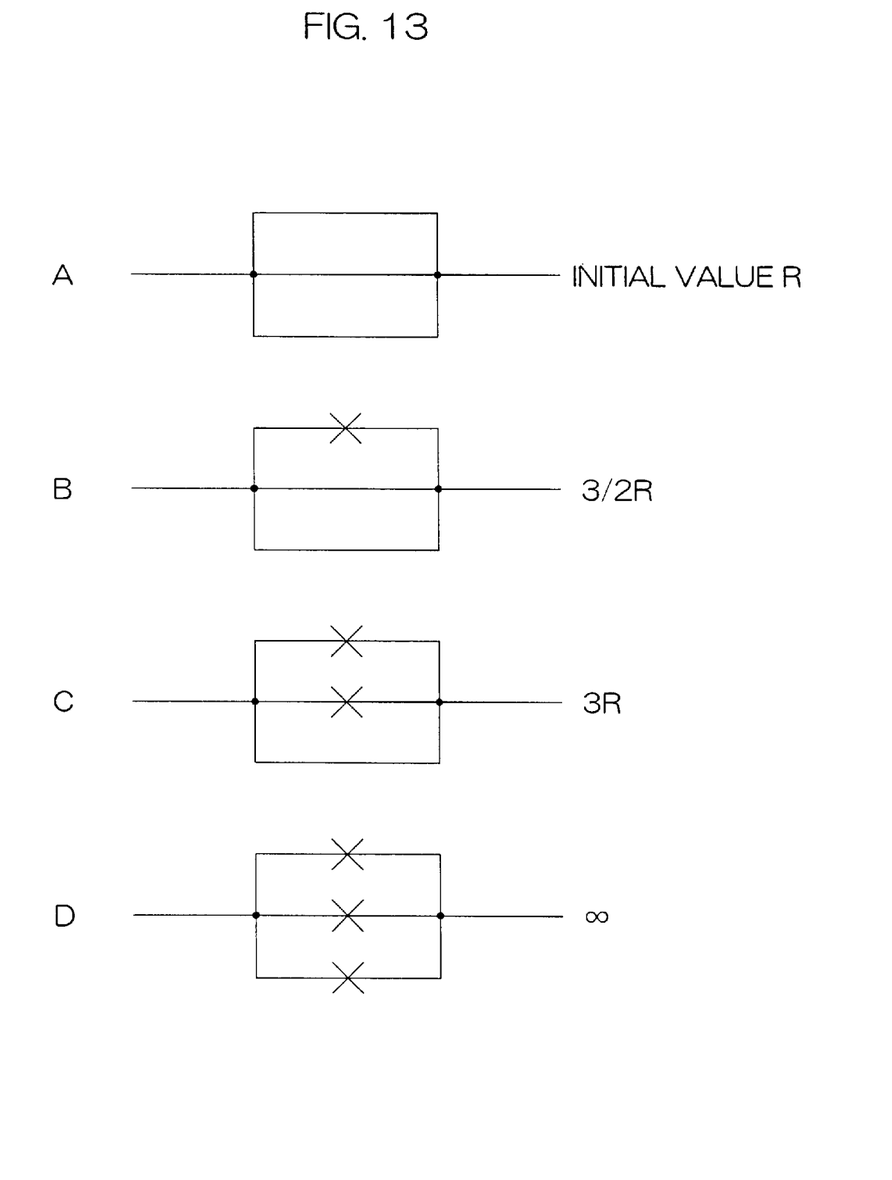
FIG. 13 is a diagram for explaining a change in resistance observed at the cut-off of each sensor line.

In this embodiment where the number of the fine lines is three, the resistance of the sensor line 10 is changed at the cut-off of each of the fine lines. An initial resistance R observed at an initial stage where the three fine lines are all conductive and yet to be abraded can be calculated from the aforesaid expression (3). Provided that the fine lines 101, 102, 103 each have the same resistance, the resistance of the sensor line 10 is changed to 3R/2, 3R and ∞ at time points of the cut-off of the respective fine lines as shown in FIG. 13. Therefore, these resistance values are employed as threshold values.

When the value of the output data of the separation filter calculated from the aforesaid expression (3) exceeds any of the threshold values, the counter is incremented by one, so that the number of the cut-off fine lines of the sensor line 10 can be determined on the basis of the counter value.

Figure 14:
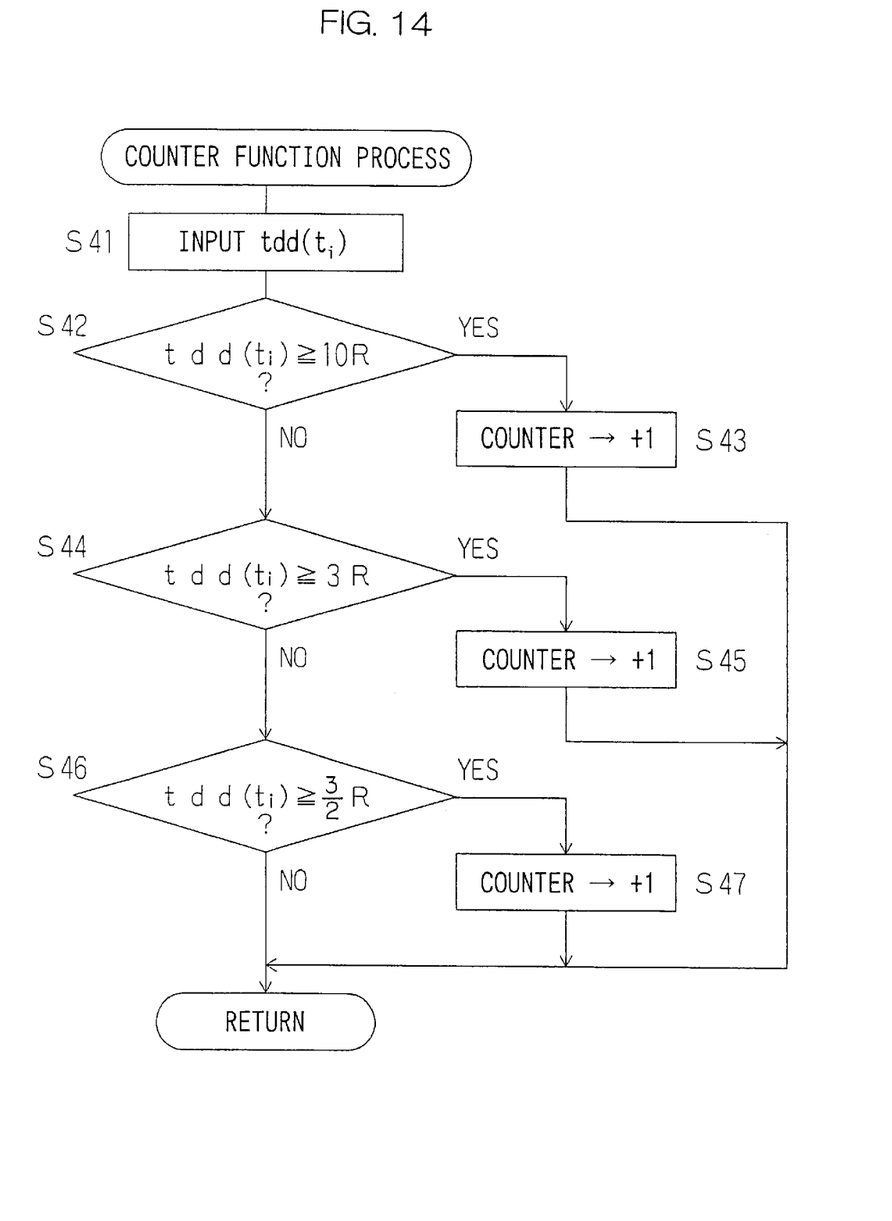
FIG. 14 is a flow chart illustrating specific operations of a counter function process.

This process will be described with reference to a flow chart in FIG. 14. In FIG. 14, the true resistance values $tdd(t_i)$ of the throw-away tip 1 obtained through the separation filtering process are time-serially inputted in Step S41. The inputted data values are each compared with the three threshold values 10R, 3R and 3R/2. The comparison is carried out in decreasing order of threshold value (Steps S42, S44, S46).

As the machining is in progress, the sensor line 10 is gradually abraded, and the resistance of the sensor line correspondingly increases. In the process shown in FIG. 14, a sequence of Steps S41→S42→S44→S46→return is repeated and, at a certain time point, a condition in Step S46 is satisfied (YES). As a result, the counter is incremented by one (Step S47), and then the process returns.

The machining further proceeds and, at a certain time point, it is judged in Step S44 that the resistance value $tdd(t_i)$ exceeds the threshold 3R. Then, the counter is further incremented by one (Step S45), so that the counter value becomes 2.

The machining still further proceeds and, at a certain time point, a condition in Step S42 is satisfied (YES). Then, the counter is incremented by one (Step S43), so that the counter value becomes 3.

The aforesaid process is expressed by the following mathematical expression, wherein the threshold is represented by $Sh_i$.

$$Sh_i = \{3/2 \cdot R, 3 \cdot R, 10 \cdot R\}, R = d(t_1) \quad (4)$$

Provided that the counter function indicative of the stepwise change is represented by $so(t_i)$, the following output is finally provided:

$$so(t_i) = \begin{cases} 0, & \text{if } tdd(t_i) < Sh_1 \\ k, & \text{if } Sh_k < tdd(t_i) < Sh_{k+1}, k = 1, 2 \\ 3, & \text{if } tdd(t_i) > Sh_3 \end{cases} \quad (5)$$

Figure 15:
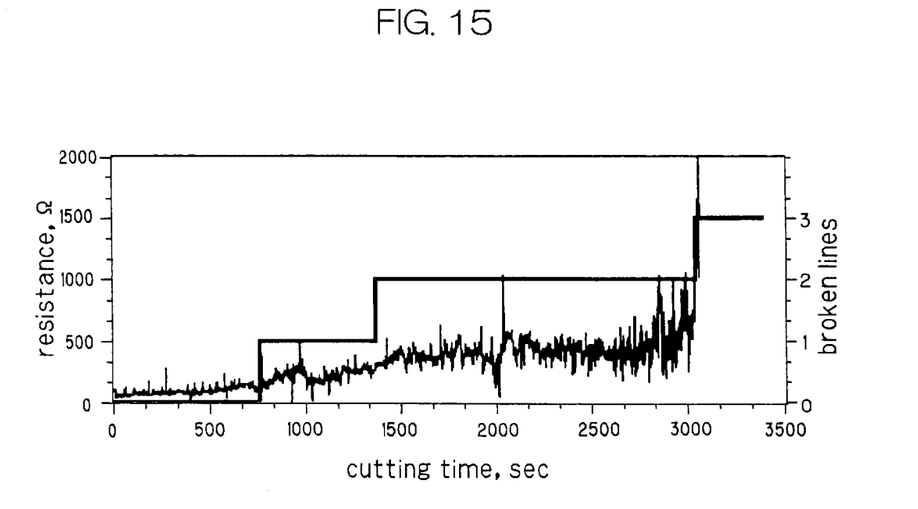
FIG. 15 is a diagram illustrating a counter function in conjunction with the sampled data.

In FIG. 15, the counter function is shown in conjunction with the sampled data shown in FIG. 4. As can be seen from FIG. 15, the counter function $so(t_i)$ counts the number of the cut-off lines at time points at which the respective fine lines 101, 102, 103 of the sensor line 10 are supposedly cut off. Thus, the effectiveness of the signal processing algorithm has experimentally been confirmed.

It should be understood that the present invention is not limited to the embodiment described above but various modifications may be made within the scope of the invention defined by the following claims. For example, the number of the fine lines of the sensor line 10 is not limited to three, but may be any number.

The number m of the sampled data to be processed in a group by the median filter is not limited to m=5. Although the data number m is preferably an odd number not smaller than 3, the data number m may be an even number. Where the data number is an even number, two median values are extracted to be averaged, and the average value is outputted as the representative value in the process.

What is claimed is:

1. A signal processing system for a cutting tool having an abrasion sensor provided on a cutting edge thereof for detecting abrasion and breakage thereof occurring due to a cutting operation, the signal processing system comprising:
    means for sampling an output of the abrasion sensor in a predetermined sampling cycle to obtain measurement data;
    noise eliminating means for eliminating a noise from the obtained measurement data;
    reduction data separating means for separating reduction data having a time-serially reduced in value from the noise-free data; and
    life expiration determining means for determining an abrasion degree and breakage of the cutting tool on the basis of process data obtained by the separation of the reduction data.

2. A signal processing system as set forth in claim 1, wherein the noise eliminating means comprises median process means for outputting a median of a predetermined number of sampled group data.

3. A signal processing system as set forth in claim 1,
    wherein the abrasion sensor comprises a plurality of sensor lines extending parallel to each other along a cutting ridge of the cutting tool,
    wherein the life expiration determining means determines the abrasion degree and breakage of the cutting tool by relating the process data to the number of the sensor lines.

4. A signal processing system as set forth in claim 3, wherein the life expiration determining means determines an initial resistance value of the plurality of sensor lines on the basis of an initial value of the process data, then determines a resistance threshold which is increased in response to cut-off of each of the sensor lines, and provides an output whenever a value of the process data exceeds the resistance threshold to indicate that the number of the cut-off sensor lines is increased.

5. A signal processing system as set forth in claim 2,
    wherein the abrasion sensor comprises a plurality of sensor lines extending parallel to each other along a cutting ridge of the cutting tool,
    wherein the life expiration determining means determines the abrasion degree and breakage of the cutting tool by relating the process data to the number of the sensor lines.

6. A signal processing system as set forth in claim 5, wherein the life expiration determining means determines an initial resistance value of the plurality of sensor lines on the basis of an initial value of the process data, then determines a resistance threshold which is increased in response to cut-off of each of the sensor lines, and provides an output whenever a value of the process data exceeds the resistance threshold to indicate that the number of the cut-off sensor lines is increased.

7. A signal processing system as set forth in claim 1, wherein the cutting tool comprises a throw-away tip provided with the abrasion sensor and a holder for holding the throw-away tip, and the abrasion sensor is capable of detecting the abrasion degree and breakage of the throw-away tip.

8. A signal processing method for a cutting tool having an abrasion sensor provided on a cutting edge thereof for detecting abrasion and breakage thereof occurring due to a cutting operation, the signal processing method comprising the steps of:

sampling an output of the abrasion sensor in a predetermined sampling cycle;

eliminating a noise from the sampled data;

separating reduction data having a time-serially reduced in value from the noise-free data; and determining an abrasion degree and breakage of the cutting tool on the basis of process data which is obtained by the separation of the reduction data and is free from time-serial reduction in value.

9. A method as set forth in claim 8, wherein the abrasion sensor comprises a plurality of sensor lines extending parallel to each other along a cutting ridge of the cutting tool, wherein the process data has a value which increases time-serially stepwise by increments associated with the number of the sensor lines.

* * * * *